US005594987A

United States Patent [19]

Century

[11] Patent Number: 5,594,987

[45] Date of Patent: Jan. 21, 1997

[54] METHOD OF MAKING A SUB-MINIATURE AEROSOLIZER

[76] Inventor: Theodore J. Century, 702 W. Carpenter La., Philadelphia, Pa. 19119

[21] Appl. No.: 519,692

[22] Filed: Aug. 28, 1995

Related U.S. Application Data

[62] Division of Ser. No. 274,234, Jul. 13, 1994.

[51] Int. Cl.$^6$ .................... B21D 53/00

[52] U.S. Cl. .................... 29/890.143; 29/456

[58] Field of Search .................... 29/890.142, 890.143, 29/456, 469

[56] References Cited

U.S. PATENT DOCUMENTS

| | | | |
|---|---|---|---|
| 539,961 | 5/1895 | Russell . | |
| 904,149 | 11/1908 | Rachmann . | |
| 1,506,721 | 8/1924 | Javorsky | 29/890.143 |
| 1,506,722 | 8/1924 | Yunker | 29/890.143 |
| 1,580,246 | 4/1926 | Heller . | |
| 1,581,223 | 4/1926 | Moore . | |
| 1,625,635 | 4/1927 | Willners . | |
| 1,899,698 | 2/1933 | Klein . | |
| 1,953,990 | 4/1934 | Roselund . | |
| 2,176,356 | 10/1939 | Paasche . | |
| 2,307,206 | 1/1943 | Fischer . | |
| 2,609,238 | 9/1952 | Anderson . | |
| 2,657,953 | 11/1953 | Hopper . | |
| 3,146,674 | 9/1964 | Wahlin | 29/890.143 |
| 3,504,893 | 4/1970 | Susuki et al. . | |
| 3,793,690 | 2/1974 | Wayne | 29/890.142 |

OTHER PUBLICATIONS

E. B. Wheeldon, M. E. Walker, D. J. Murphy & C. R. Turner, Intratracheal aerosolization of endotoxin in the rat: a model of the adult respiratory distress syndrome (ARDS), Departments of Experimental Pathology and Investigate Toxicology, SmithKline Beecham Pharmaceuticals, King of Prussia, PA 19406 [Laboratory Animals (1992) 26, pages 29–37].

*Primary Examiner*—David P. Bryant
*Attorney, Agent, or Firm*—Paul & Paul

[57] ABSTRACT

A sub-miniature aerosolizer comprises a substantially elongated sleeve member, a substantially elongated insert and a substantially elongated body member. The sleeve member includes a threaded inner surface which is adapted to receive the insert which is a correspondingly threaded member. The threaded insert provides a substantially helical channel. The body member includes a cavity on its first end which terminates by an end wall at its second end. The end wall includes an orifice extending therethrough. The body member is connected with the sleeve member to provide the sub-miniature aerosolizer of the present invention. The sub-miniature aerosolizer is sized to accommodate insertion into the trachea of a subject for use of the device. For operation of the device, the sub-miniature aerosolizer is connected by a suitable tube with a liquid pressure driver apparatus. The liquid pressure driver apparatus is adapted to pass liquid material therefrom which is sprayed from the sub-miniature aerosolizer. Due to the location of the device deep within the trachea, the liquid material is sprayed in close proximity to the lungs, with resulting improved penetration and distribution of the sprayed material in the lungs.

4 Claims, 4 Drawing Sheets

METHOD OF MAKING A SUB-MINIATURE AEROSOLIZER

CROSS-REFERENCE TO RELATED APPLICATIONS

This Application is a division of U.S. Pat. application Ser. No. 08/274,234 filed Jul. 13, 1994.

BACKGROUND OF THE INVENTION

1. Field of the Invention

The present invention relates generally to the administration of drugs and drug therapy and more particularly to the introduction of drugs into the lungs.

2. Description of the Prior Art

Several recent therapeutic developments entail the administration of drugs directly into the lungs. These include, for example, 1) the introduction of altered adenovirus in the "gene therapy" treatment of cystic fibrosis, 2) the use of surfactant in the treatment of pediatric and adult respiratory distress syndrome (ARDS), and 3) the introduction of antibiotics, antibodies, and other drugs.

Patients requiting the administration of drugs to the lungs face limited options. The most common approach, that of introducing a large liquid bolus directly into an endotracheal tube with a syringe, entails a number of drawbacks:

To optimize the uniformity of distribution of the bolus, the patient must often be rotated, The large liquid load can lead to severe respiratory complications, and The large amount of material required can lead to considerable expense.

A recent experimental approach is that of introducing ultrasonically nebulized material to the endotracheal tube via a "T" connection. While much lower amounts of such nebulized material have been found effective for treatment, this technique also has serious drawbacks:

The efficiency of delivery is very low; only about 2% of the material introduced into the nebulizer actually remains in the lungs, Many drugs cannot be nebulized effectively, Achievement of a uniform distribution of material in the lungs remains problematic, and The protocol for use of the nebulizer is relatively complex.

These considerations point to the desirability of a device for delivering drug solutions directly into the lungs. In particular, such a device would be:

capable of delivering a spray of fine particles for deep penetration and broad distribution in the lungs, small and flexible enough to be inserted into an endotracheal tube, endoscope, or other intratracheal device, or directly into the trachea so as to minimize losses of drug material to the mouth, throat and trachea, of the liquid-pressure type of sprayer so as to avoid those problems associated with the common air-pressure type of sprayer, particularly the unwanted generation of a large mount of vehicle gas which may be injurious to the lungs.

The present invention has been developed in view of the foregoing and to overcome the deficiencies of the prior art.

SUMMARY OF THE INVENTION

The present invention provides a novel administration device adapted for delivering drug solutions directly into the lungs. For this purpose, the present invention provides a sub-miniature aerosolizer sized for intratracheal insertion which is adapted for spraying a liquid material therefrom in close proximity to the lungs. The sub-miniature aerosolizer is placed into connection with a liquid pressure driver apparatus for delivering of the liquid material. In accordance with the present invention, the sub-miniature aerosolizer comprises a generally elongated sleeve member which defines a first end and a second end and includes a longitudinally extending opening therethrough. The first end of the sleeve member is placed in connection with the liquid pressure driver apparatus. A generally elongated insert is also provided. The generally elongated insert defines a first end and a second end and is received within at least a portion of the longitudinally extending opening of the sleeve member. The insert includes an outer surface which has at least one substantially helical channel provided surrounding its outer surface which extends from the first end to the second end. The substantially helical channel of the insert is adapted to pass the liquid material which is received by the sleeve member. A generally elongated body member is also included which is in connection with the sleeve member. The body member includes a cavity provided in its first end which terminates at an end wall which is adjacent its second end. The end wall is provided having an orifice therein for spraying the liquid material which is received from the insert. The portions of the sleeve member, insert and body member, in combination, are of sufficient size for intratracheal insertion.

The present invention also provides a method of using the sub-miniature aerosolizer described above. The method includes the steps of connecting the sub-miniature aerosolizer with a first end of a hollow tube member and connecting the second end of the hollow tube member with the liquid pressure driver apparatus. The method further includes the steps of providing the sub-miniature aerosolizer in the trachea or into a member which is provided in the trachea, and then activating the liquid pressure driver apparatus for spraying a liquid material therefrom.

The present invention also provides a method of making a liquid sprayer aerosolizer adapted for being placed in connection with a liquid pressure driver apparatus for delivery of liquid material. For this purpose, the method includes the steps of providing an appropriate length of a first hollow tube member and forming a threaded area in a portion of an inner surface of the first hollow tube member. The method further includes the steps of providing a screw member, grinding substantially flat a first end of the screw member and forming a substantially elongated slot within the substantially flat first screw end. The method also includes the steps of inserting the substantially flat first end of the screw member into a first end of the first hollow tube member, providing a driver on the opposite end of the first hollow tube member for engaging the substantially elongated slot within the first screw end and then rotating the driver for backing the screw member into the first hollow tube member for engagement of the threaded area thereof. Further, the method includes the steps of providing an appropriate length of a second hollow tube member and also a foil disc, and then coupling the foil disc to a first end of the second hollow tube member. In addition, the method includes the steps of drilling a hole through the foil disc, deburring an appropriate amount around the hole on each side of the disc and then coupling together the first and second hollow tube members.

In accordance with the present invention, an object is to provide a spray device of sufficient size to permit insertion into an endotracheal tube, bronchoscope or into the trachea directly.

It is another object of the present invention to provide an intratracheal spray device capable of delivering an effective amount of material in a short length of time.

It is another object of the present invention to provide an intratracheal liquid spray device capable of producing relatively small droplets and at relatively low pressures.

It is still a further object of the present invention to provide an intratracheal spray device which is easy to operate and clean.

These and other objects and advantages of the present invention will become more apparent when taken into consideration with the following description and the attached drawings.

DETAILED DESCRIPTION OF THE PREFERRED EMBODIMENTS

Figure 1:
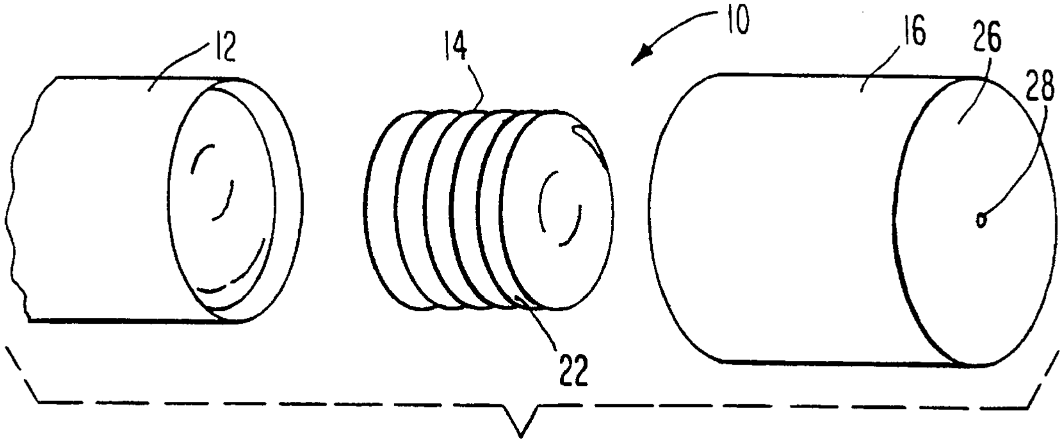
FIG. 1 is an exploded side elevational view of the elements of a sub-miniature aerosolizer of the present invention.

Referring now to the drawings in detail, wherein like reference numerals indicate like elements throughout the several views, there is shown in FIG. 1 an exploded side elevational view of the elements of the sub-miniature aerosolizer 10 in accordance with the present invention. The sub-miniature aerosolizer 10 as shown includes, as portions thereof, a generally elongated sleeve member 12, a generally elongated insert 14, and a generally elongated body member 16.

Figure 2:
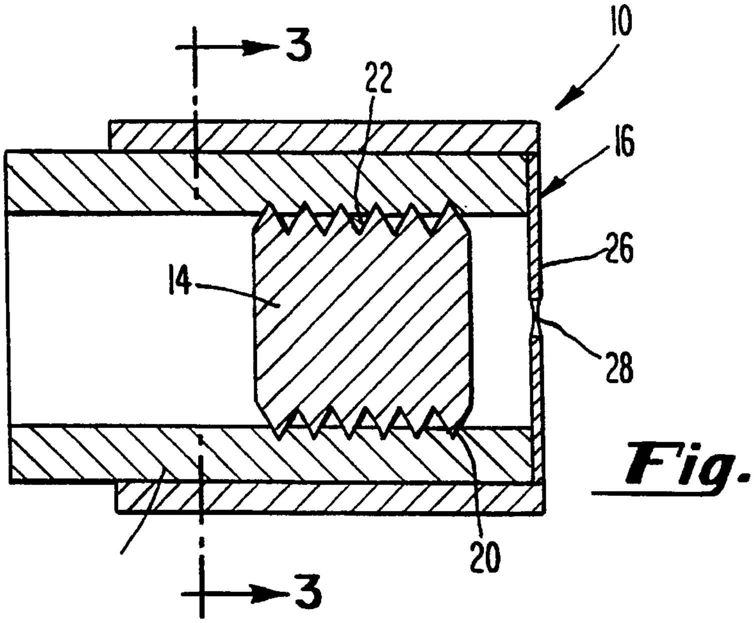
FIG. 2 is a sectional side elevational view of the sub-miniature aerosolizer of FIG. 1 shown assembled.

The generally elongated sleeve member 12 as illustrated is comprised of a hollow tube member, which in the present invention is 18-gauge 316 stainless steel, however, other suitable materials can also be used. The sleeve member 12 can be of any sufficient length, and this will usually vary depending on the application of the sub-miniature aerosolizer, for example, for adult or infant persons, or for animal use, such as for rats which would be set at 3" and for guinea pigs which would be set at 4". In the present embodiment, the outer diameter of the tubing is set at 0.05" and the inner diameter of the tube is set at 0.033", however, this could be varied where desired. As best seen in FIG. 2, the sleeve member 12 is further provided with a threaded channel 20 provided within its inner surface and adjacent a second end thereof, the purpose of which will be described below.

Figure 3:
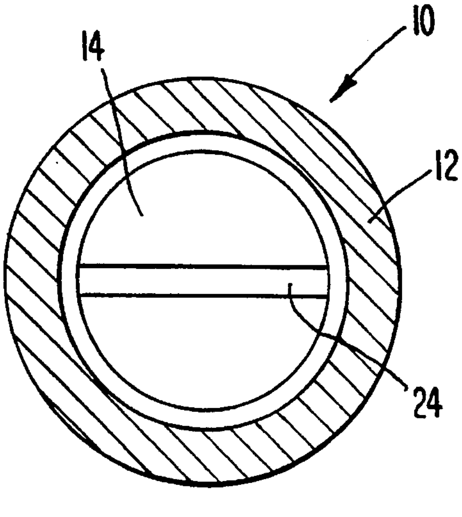
FIG. 3 is a sectional rear elevational view of the sub-miniature aerosolizer of FIG. 2 taken along the line 3—3.

The insert 14 as illustrated comprises a generally elongated member having a substantially helical-shaped channel 22 provided along the length thereof, as is best seen in FIG. 1. The substantially helical channel 22 defines a series of alternating raised and lowered sections provided on its outer surface. As illustrated in FIG. 3, the insert 14 is further included with a substantially elongated slot 24 provided within its first end. In the present embodiment, the composition of the insert 14 is preferably of 316 stainless steel; however, other suitable materials could also be provided without departing from the spirit of the invention. The operation of the insert 14 will be described in more detail below.

The body member 16, as best seen in FIG. 1, is also comprised of a hollow tube member. A first end of the body member 16 is provided with a cavity extending therein which terminates by an end wall 26 provided adjacent its second end. In accordance with the present invention, the end wall 26 is provided with an orifice 28 extending through the length thereof. As best seen in FIG. 2, the configuration of the orifice 28 in the present embodiment preferably includes a central area of substantially constant diameter, and areas which are tapered or substantially conical-shaped at each end thereof. In accordance with the present embodiment, the body member 16 is preferably comprised of 17-gauge extra-thin wall 316 stainless steel tubing, which includes an outer diameter of 0.058" and an inner diameter of 0.050". It should be understood, however, that other suitable materials, and of any desired configuration, can also be utilized for this same purpose.

On assembly, as indicated in FIG. 2, generally the insert 14 is first placed within the sleeve member 12, and then the sleeve member 12 and body member 16 are connected to each other to form the aerosolizer 10. As indicated earlier, a primary object of the present invention is to provide a sub-miniature aerosolizer; in particular, one which is sufficiently small for intratracheal insertion, such as into an endotracheal tube, bronchoscope, or into the trachea directly. In accordance with this aspect of the present invention, a novel method for making such a device has been developed. In accordance with this method, the threaded channel 20 provided in the sleeve member 12 is tap formed in the inner surface. For this purpose, the end of the sleeve member 12 is also preferably drilled or bored to an inner diameter of 0.036" for a distance of 0.100" prior to providing the threaded channel 20, afterwhich, the bored end is preferably tapped with a 1 mm×0.025 mm taper tap sufficient to provide a space of 0.020" length between the second end of insert 14 and the second end of sleeve member 12.

The insert 14 is also preferably manufactured from standard stock material, which in this embodiment is a 1 mm×0.025 mm 316 stainless steel screw. For this purpose, the screw is first cut preferably to a length of 0.040" and then ground flat to 0.030". The substantially elongated slot 24 is then formed within the grounded end preferably with a 0.008" slitting saw to a depth of 0.006". Afterwhich, the slot 24 can be deburred if desired per use of a suitable small tool under a microscope.

The body member 16, as indicated above, preferably is provided by cutting and deburring 0.050" length of the 17-gauge extra-thin-wall 316 stainless steel tubing to a configuration consisting of 0.058" outside diameter by 0.050" inside diameter. The end wall 26 is preferably formed from suitable sized discs, preferably 0.002" in thickness in the present embodiment, which are punched out of 316 stainless steel foil, with a suitable punch and die set. Thereafter, the disc is secured against one end of the body member 16 for providing the end wall 26.

Figure 9:
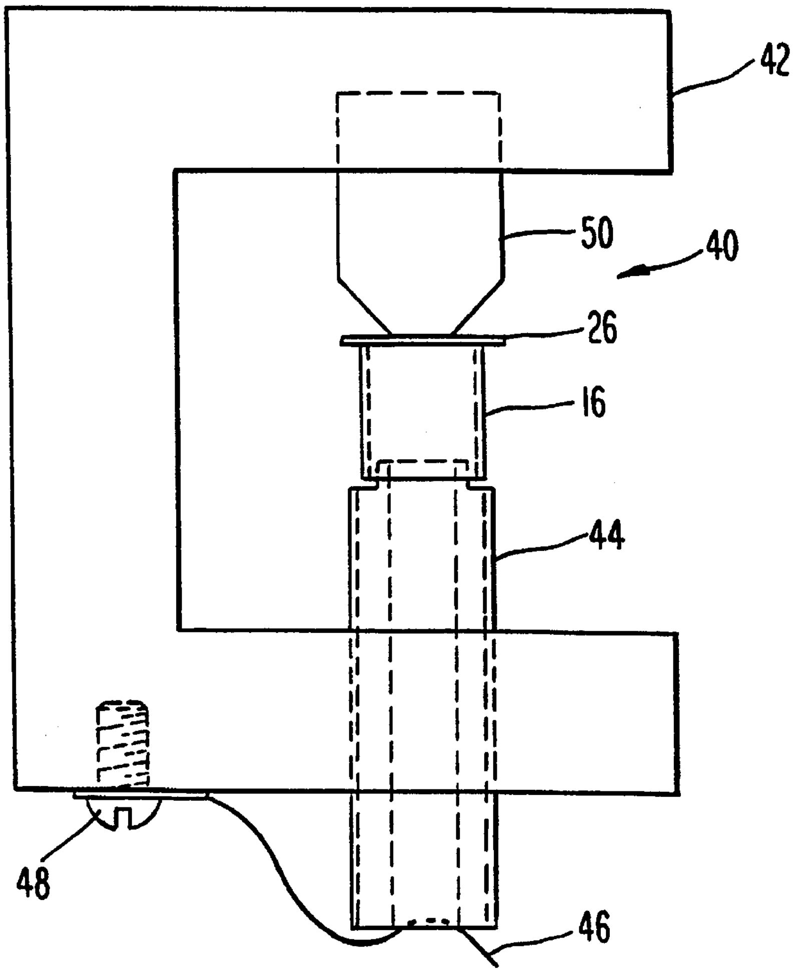
FIG. 9 is an elevational view of a fixture used in the connection of a portion of the elements of the sub-miniature aerosolizer of FIG. 1.

The installation of the disc to the body member 16 is carried out via utilization of a special fixture 40, as is shown in FIG. 9. The fixture serves to hold the disc and body member in register and is designed so as to minimize heat loss during the brazing operation. The fixture includes, as portions thereof, a substantially U-shaped frame 42 comprising a first wall connected to and at spaced separation from a second wall via a connecting member. The first wall includes formed or otherwise provided therein an aperture for receipt of a first contact member 44. The first contact member 44 is slidably disposed within the aperture in the first wall as will be described below. A biasing member comprising a spring 46 is also provided secured to the frame 40 by a screw 48 or other suitable fastening device. The spring 46 engages and biases the first contact member 44 in a direction of the second wall of the frame 42. The second wall of the frame 42 includes a second contact member 50 extending outwardly therefrom. Preferably, the second contact member 50 is fixed in relation to the frame 42 through engagement of a correspondingly configured aperture provided within the second wall thereof, however, other means can also be utilized for this same purpose. Also, in the present embodiment, the second contact member 50 is preferably comprised of a ceramic material at least at its distal end. The distal end of the second contact member 50 is also substantially planar for engagement of the foil disc forming the end wall 26. The first contact member 44 is preferably comprised of tubular stainless steel and is included with a substantially annular boss extending from its distal end for coaxial engagement of the cavity provided in the first end of the body member 16. In this manner, upon assembly the foil disc is maintained in contact with the body member 16 through the bias of the spring 46 on the first contact member 44. In this position, the foil disc can be secured with the body member 16 through application of suitable adhesive, for example, silver brazing alloy in the present embodiment such as Harris No. 50N (Solidus 1220° F., Liquidus 1305° F.). The ceramic and tubular stainless steel materials of the contact members operate to inhibit the conduction of heat away from the body member 16 and foil disc. The body member 16 with attached end wall 26 are then removed from the fixture 40 and preferably are cleaned and inspected under a microscope to ensure proper adhesion.

The next step is to provide the orifice 28 through the foil disc end wall 26. For this procedure, preferably 0.045" diameter discs are first punched out of a sheet of material which is sufficiently hard to prevent "break-through" of the drill during the drilling process. In this embodiment, preferably 0.010" thick brass sheet is utilized. Under a microscope, the brass disc is placed on top of a mandrel coaxial to the spindle of a micro drill press before setting the body member 16 in place on the mandrel. The end wall 26 is then drilled preferably with a 0.0047" or 0.0019" diameter drill and thereafter removed and deburred on each end with a small center drill.

For installation of the screw insert 14 within the sleeve member 12, the insert 14 is first installed with the slotted end first in the second end of the sleeve member 12 in order to engage the threaded channel area 20. A special screwdriver, preferably comprising a 0.032" diameter of stainless steel wire with a 0.008" blade on its end, is inserted into the opposite end of the sleeve member 12 in order to engage the slot 24 to back screw the insert 14 into the threaded channel 20 for engagement of this member. To facilitate this procedure, preferably the aforementioned process is carried out under a microscope. Subsequently, if the threaded channel 20 portion of the sleeve member 12 is such that the insert 14, when installed, results in there being a distance between the second (unslotted) end of the insert 14 and the end of the sleeve member 12 of greater than 0.020", additional grinding and deburring of the front of the sleeve member 12 can be carried out to provide suitable fit. However, if such should be too shallow, the insert 14 can be unscrewed and a deeper tap provided in the inner sleeve surface.

For completion of the assembly of the aerosolizer 10, the sleeve member 12 is connected with the body member 16. Preferably, for this purpose, the body member 16 is placed on the end of the sleeve member 12 and a suitable amount of adhesive material, preferably solder such as Harris Stay-Brite Silver-Bearing Solder (melting point 430° F.) is provided.

Based on the foregoing method, it should be understood that an aerosolizer is provided which is sufficiently small to allow installation for intratracheal use, such as in an endotracheal tube, bronchoscope or in the trachea directly. In the present embodiment, for This purpose, the dimensions are preferably 0.059" in diameter by 1/16" (0.0625") in length, which is sufficiently small for this purpose. However, it should be understood that other dimensions can also be used for this same purpose.

Figure 4:
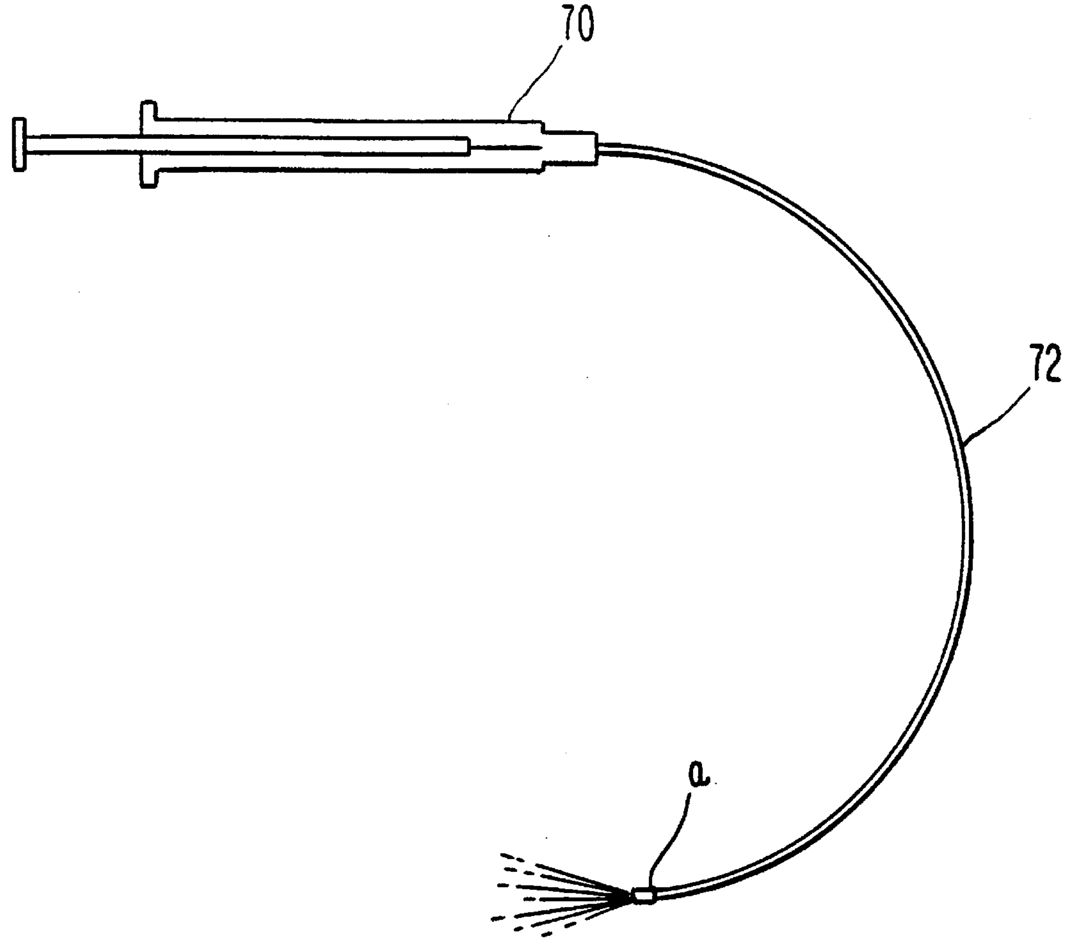
FIG. 4 is an elevational view of the sub-miniature aerosolizer of FIG. 1 illustrating the operation thereof in connection with a syringe by a flexible plastic tube.
Figure 4A:
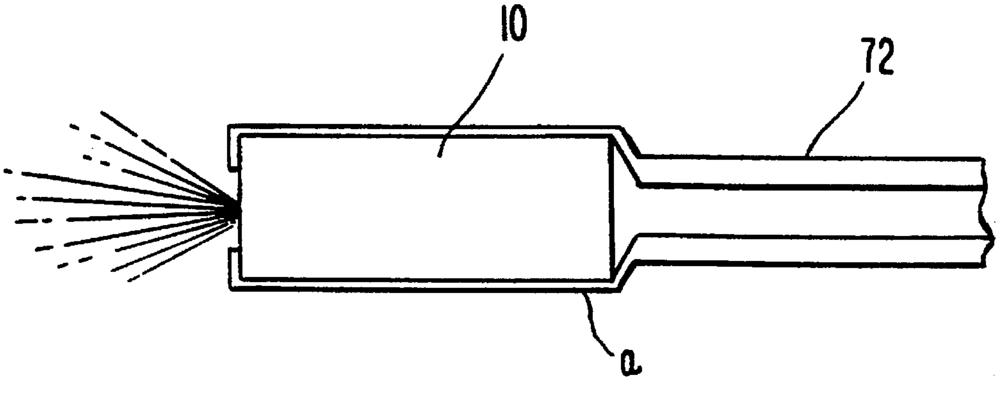
FIG. 4*a* is an enlarged view illustrating the position of the sub-miniature aerosolizer in relation to the flexible plastic tube.

The aerosolizer 10 according to the present invention is brought into connection with a suitable liquid pressure driver apparatus for use, for example, in the manner illustrated in FIGS. 4–8. FIG. 4 illustrates the aerosolizer 10 in connection with a conventional hand-held syringe 70. In this illustration, a flexible plastic tube 72, such as PEEK (polyetheretherketone), Teflon, FEP (fluorinated ethylene propylene) or Tefzel can be utilized for connection of the aerosolizer 10 to the syringe 70. In accordance with the present invention, any tubing with sufficiently small o.d. can be utilized which has a heavy enough wall to withstand the pressures that can be produced by the syringe (approximately 300 to 400 psi) and still be moderately flexible for suitable operation. In this embodiment, the dimensions of the tubing are preferably 1/16" outer diameter by 0.030" inner diameter. As illustrated in FIG. 4 at "a" and in the enlarged view of FIG. **4*a*, preferably the aerosolizer 10 for connection is inserted in the hollow portion of the tube 72 at its second end opposite the syringe 70. For this purpose, preferably the end of the plastic tube is drilled or otherwise bored out to 0.050" for a distance of about 0.100" and the aerosolizer is then pushed into the tube. Afterwhich, preferably, the end of the tube is formed around the device 10** to ensure a secure encapsulation. For example, a hot spatula can be used in order to form the end of the plastic tubing to provide a lip on the end thereof.

Figure 5:
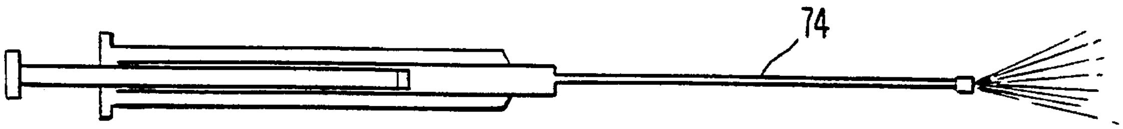
FIG. 5 is an elevational view illustrating the operation of the sub-miniature aerosolizer of FIG. 1 in connection with a syringe by a stainless steel tube.
Figure 6:
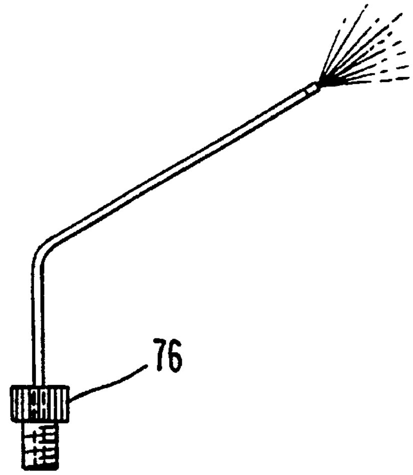
FIGS. 6 and 7 are elevational views illustrating a chromatography fitting and luer hub, respectively, as alternate configurations for attachments to other types of syringes and illustrates examples of other configurations of the tubes illustrated in FIGS. 4 and 5.
Figure 7:
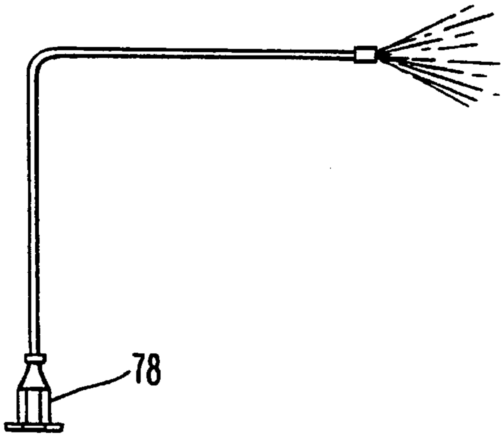
Figure 8:
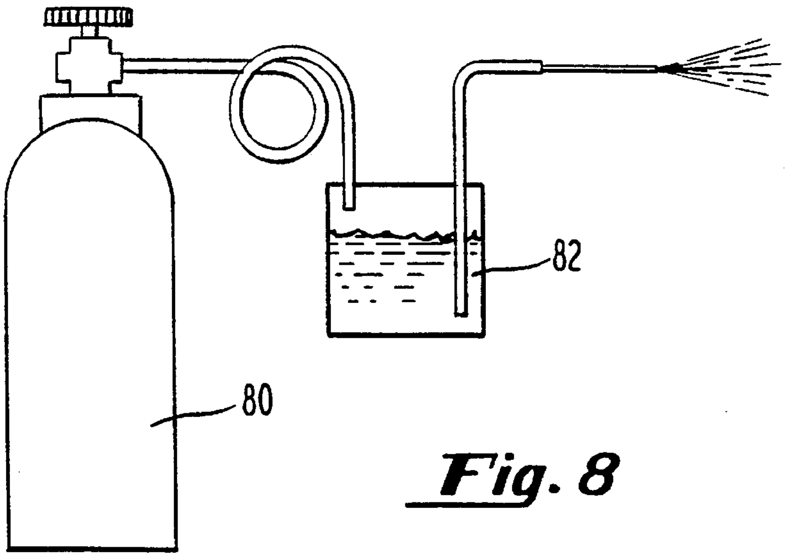
FIG. 8 is an elevational view of the sub-miniature aerosolizer of FIG. 1 shown in a configuration connected with a source of compressed gas.

FIG. 5 is another illustration of the aerosolizer 10 in connection with a hand-held syringe; however, in connection therewith by a stainless steel tube 74. In this arrangement, preferably, the stainless steel tube 74 is formed as a part of the sleeve 12 and of any desired length, and then connected with the syringe in the manner shown. FIGS. 5 and 6 are additional examples which illustrate some additional hub configurations for connection with other suitably configured syringe devices. For example, FIG. 6 illustrates connection by a 1/4–28 chromatography fitting 76 and FIG. 7 illustrates a luer hub arrangement 78. Further, these examples also illustrate that the plastic or stainless steel tubing can be provided in any suitable configuration depending on the desired use of the device. Generally, the plastic tubing arrangement is best suited for use in human applications or other applications where it is necessary to insert the device through a given small passage and flexibility of the tube 72 is important. For example, in a typical use for human application, the individual is already intubated with an endotracheal tube or bronchoscope and the aerosolizer 10 is then merely inserted into the existing tube structure. Alternatively, the plastic tubing can be inserted directly into the patient's trachea in order to effect the spraying procedure, provided a local anesthetic were applied beforehand. Typically, the arrangement of the stainless steel tubing has been best suited for animal use where an animal has been previously anesthetized, however, such could also be used for other purposes as well, such as in human subjects if so desired.

As indicated earlier, the aerosolizer device 10 of the present invention can be utilized for providing any variety of liquid materials into the lung. In this manner, the liquid materials would be passed from the liquid pressure driver apparatus to the patient. Generally, with a hand-held syringe, the volume of material which can be suitably sprayed is in the order of 0.5 to 1 ml, which is the largest syringe with which an ordinary person is capable of generating enough pressure to produce a sufficient spray. In other circumstances, for example, where a continuous spraying of material is desired, the device can also be attached to any suitable high pressure device, such as that illustrated in FIG. 8. In this arrangement, the sprayer is connected with a source 80 of a suitable compressed gas, such as air, for delivery of the liquid material identified by 82. In some particular circumstances, using oxygen as the compressed gas, the liquid material being sprayed into the lungs will have a relatively high oxygen content which, when released in the lungs, may have additional therapeutic advantages.

In view of that set forth above, it should be understood that the design of the aerosolizer of the present invention possesses several advantages over conventional devices. In particular, an advantage is that the arrangement of the substantially helical channel 22 in the insert 14 provides the characteristics of a pressure-swirl type of atomizer known in the art. Generally, a pressure-swift type of device is capable of producing relatively small droplets at relatively low pressures. In accordance with the present invention, in this manner the present device produces droplets of about 25 microns mass mean diameter at the pressures available in a typical 500 microliter gas-tight syringe (300 to 400 psi). Further, the imposition of the insert 14 between the liquid pressure head and the orifice 28 serves both to increase the kinetic energy of the fluid in the sprayer head and to impart angular momentum to the emerging particles, thus increasing the spray cone angle, a critical aspect of achieving small droplet sizes. In the present invention, the insert 14 is also designed and fabricated so as to be effective at the micro level. In addition, an advantage is that the insert 14 is also fabricated from standard stock material which further facilitates the manufacturing process.

Further, the length/diameter ratio of the orifice 28 is also a sensitive, directly proportional determinant of droplet size, as is the diameter of the orifice 28 itself. Another advantage of the present invention is to provide a highly favorable length/diameter ratio of 0.426 (0.002"/0.0047"), and the conical deburring operation may also further improve this number to 0.213. Further, another advantage is to provide the orifice 28 precisely coaxially with the center of the insert 14, which is another sensitive determinant of spray quality.

The methodologies of the present invention enable these aspects of sprayer head design to be realized at the micro level.

Furthermore, still another advantage is in the liquid pressure-driven design. In particular, unlike the common type of air pressure-driven ("venturi") sprayers, the present liquid pressure-driven design eliminates the need for a large volume of vehicle air. In the present device, the size and geometry of the-spray plume is strictly determined by the kinetic energy of the emerging particles and the spray cone angle; that is, by the ease with which the spray particles can escape from the sprayer tip into the ambient air. As indicated above, the spray cone angle is improved by deburring portions on both the inside and the outside of the end wall 26. As a result of this arrangement, very little momentum is transferred from the impacting droplets to the surface upon which they are deposited as the relatively high surface-to-volume spray is converted into a lower surface-to-volume sheet coveting the target. This accounts for the uniform distribution of the material, as well as for the "softness" of the spray.

Additionally, as indicated above, another advantage is in the capability of the device to be inserted down an endotracheal tube, bronchoscope, or similar device in an intubated patient or, with local anesthetic, into the trachea directly. In particular, since the spray from the device is introduced directly into the lungs, as opposed to being breathed in from the outside as is the case with an inhaler, losses due to deposition on the walls of the nasal passages, mouth, throat and trachea are avoided. In addition, the droplet sizes of such a device are somewhat larger than those produced by an ultrasonic nebulizer (25 microns versus 2 microns). As a result, the droplets are less likely to be exhaled, thus leading to a delivery efficiency of virtually 100%. Furthermore, delivery of drug material in the form of a fine spray in close proximity to the lungs leads to a highly uniform pattern of distribution. Further, due to the foregoing advantages, only a small fraction of the material previously required need be used for effective treatment, which is of particular significance with many materials which are rather difficult to manufacture and/or costly to produce. Additionally, the present device is capable of delivering an effective dosage of 1 cc of material per minute.

It will be recognized by those skilled in the art that changes may be made by the above-described embodiments of the invention without departing from the broad inventive concepts thereof. For example, the aerosolizer device 10 in accordance with the present embodiment is disclosed as preferably being comprised of stainless steel. However, it should be understood that other suitable materials can also be provided for the same purpose. In particular, all of the elements of the aerosolizer device 10, for instance, the sleeve member 12, insert 14 and body member 16 (including the end wall 26) can all be manufactured of plastic for the same purpose. An advantage of such a design is that the plastic tubing for connection to the syringe, as illustrated in FIG. 4, can be provided as an integral portion of the sleeve 12, similar to the stainless steel tube illustrated in FIG. 5, rather than being provided as a separate element.

Furthermore, as illustrated in the present embodiment, the orifice 28 is described as comprising a hole preferably 0.002" in length provided through the end wall 26. However, it should be understood that the orifice can be of any suitable size or configuration. For instance, the orifice can also be provided being annular in shape for the same purpose.

It should be understood, therefore, that this invention is not limited to the particular embodiments disclosed, but it is intended to cover all modifications which are within the scope and spirit of the invention as defined by the appended claims.

What is claimed is:

1. A method for making a liquid sprayer aerosolizer adapted for being placed in connection with a liquid pressure driver apparatus for delivery of liquid material, said method including the steps of:

providing an appropriate length of a first hollow tube member having a specified outer diameter defined by an outer surface and a specified inner diameter defined by an inner surface;

tapping a threaded area in a portion of said inner surface of said first hollow tube member a predetermined distance from a first end thereof;

providing a screw member of an appropriate diameter and length;

grinding substantially flat a first end of said screw member;

forming a substantially elongated slot within said substantially flat first end of said screw member;

inserting said substantially flat first end of said screw member into said first end of said first hollow tube member;

providing a driver in a second end of said first hollow tube member for engaging said substantially elongated slot within said substantially flat first end of said screw member;

rotating said driver for backing said screw member into said first hollow tube member through engagement of the threaded portions thereof;

providing an appropriate length of a second hollow tube member having a specified outer diameter defined by an outer surface and a specified inner diameter defined by an inner surface;

providing a foil disc of specified diameter and thickness defined by first and second sides;

coupling said foil disc to a first end of said second hollow tube member;

drilling a hole through said foil disc from the first side through to the second side thereof;

deburring an appropriate amount of said first and second sides of said foil disc proximate said hole therethrough; and coupling said first and second hollow tube members.

2. A method according to claim 1, wherein the step of coupling said foil disc to a first end of said second hollow tube member includes the steps of:

inserting said foil disc and said second hollow tube member into a fixture, said fixture exerting an appropriate amount of pressure against said second hollow tube member proximate a second end thereof and against said foil disc on the side opposite that engaging said first end of said second hollow tube member adapted for retaining said foil disc in contact with said second hollow tube member; and attaching said foil disc to said second hollow tube member.

3. A method according to claim 1, Wherein the step of drilling a hole through said foil disc from the first side through to the second side further includes the steps of:

providing a disc of specified diameter and thickness of a suitable material;

placing said disc of suitable material behind said second side of said foil disc prior to drilling said hole therethrough to prevent drill break-through.

4. A method according to claim 1 further including the step of providing said aerosolizer of sufficient size for intratracheal insertion.

* * * * *